United States Patent [19]

Bunnell et al.

[11] Patent Number: 5,328,446
[45] Date of Patent: Jul. 12, 1994

[54] ORTHOPEDIC JOINT AND METHOD FOR TREATING A CONTRACTURE

[75] Inventors: William P. Bunnell, 1590 Edge Hill La., Redlands, Calif. 91373; James K. Rasmusson, Birmingham, Mich.; Steven R. Lamb, Pleasanton, Calif.

[73] Assignees: Becker Orthopedic Appliance Company, Troy, Mich.; William P. Bunnell, Redlands, Calif.

[21] Appl. No.: 968,542

[22] Filed: Oct. 29, 1992

[51] Int. Cl.⁵ .................................................. A61F 5/00
[52] U.S. Cl. ...................................... 602/16; 482/131; 482/907; 602/26
[58] Field of Search ............. 602/5, 16, 20, 23, 26; 482/131, 907

[56] References Cited

U.S. PATENT DOCUMENTS

| 2,832,334 | 4/1958 | Whitelaw . | |
|---|---|---|---|
| 4,456,247 | 6/1984 | Ehrenfried . | |
| 4,718,665 | 1/1988 | Airy et al. | 602/16 |
| 4,768,498 | 9/1988 | Herrick | 602/32 |
| 4,899,735 | 2/1990 | Townsend et al. | 602/20 |
| 5,031,606 | 7/1991 | Ring, Sr. . | |
| 5,052,379 | 10/1991 | Airy et al. | 602/16 |
| 5,100,403 | 3/1992 | Hotchkiss et al. | 602/16 X |
| 5,103,807 | 4/1992 | Makaran | 602/21 X |
| 5,121,747 | 6/1992 | Andrews | 602/16 X |
| 5,137,504 | 8/1992 | Mangini | 482/131 |

OTHER PUBLICATIONS

BODI Brochure published at least as early as Oct. 26, 1992.

Primary Examiner—Richard J. Apley
Assistant Examiner—Linda C. M. Dvorak
Attorney, Agent, or Firm—Jenner & Block

[57] ABSTRACT

A joint device is provided for treating a patient who is unable to flex and extend an arm, leg or other jointed member through its normal range of movement about the patient's joint. The joint device includes two extending sidearms. Each sidearm is secured by a sleeve, cast, brace or the like to the patient's limb so that the sidearms are on opposite sides of the afflicted joint. The joint device pivotally connects the two sidearms, and includes a selectively actuated one-way clutch which allows movement in one direction while inhibiting it in the other.

6 Claims, 3 Drawing Sheets

ORTHOPEDIC JOINT AND METHOD FOR TREATING A CONTRACTURE

FIELD OF THE INVENTION

This invention relates to orthopedics generally, and more specifically to joints for treating contractures and like disorders.

BACKGROUND OF THE INVENTION

In the body, limbs are moved by opposing muscle pairs such as the biceps and triceps muscles. For example, a person's arm is flexed by contraction of the biceps, and extended by contraction of the triceps. The arm may lose its full or normal range of flexion or extension movement. For example, a patient suffering from a contracture might be unable to fully extend his or her arm because the patient's biceps do not extend sufficiently to allow the triceps to straighten the arm.

To treat these ailments, a number of techniques have been devised. In accordance with one known technique, a brace is applied to the afflicted limb. By means of a spring or the like, a constant force is applied to the brace, urging the patient's limb toward extension or flexion. Thus, in the case where a patient is unable to fully extend his or her arm, the existing technique applies a force urging extension. Over time, this force stretches the biceps, allowing the triceps to extend the arm. Understandably, however, this technique may cause the patient some discomfort.

A need exists for other methods and apparatus for treating contractures and similar disorders.

SUMMARY OF THE INVENTION

It is therefore an object of the present invention to provide a novel and useful joint for use with a splint, cast, brace or the like. The joint is especially suited for treating an ailment (or "contracture") which makes a patient unable to flex and extend an arm, leg or other jointed member through its normal range of movement about the patient's joint.

For purposes of this specification, the term "jointed member" shall mean any member of the body, including a limb, neck or back, which is capable of movement about a joint. The term "afflicted direction" shall mean the direction of extension or flexion movement which the patient, due to his ailment, is unable to move. The term "contracture" shall mean any injury, disorder or affliction, however caused, which limits the range of movement of a jointed member about a patient's joint.

In the preferred embodiment, two sidearms are attached to and extend from the joint device for pivoting movement about the joint device. The sidearms may be secured to the joint device in any suitable manner, such as screws, rivets and can be integrally formed as part of the joint device. Each sidearm is secured by sleeves, casts, braces or the like to the patient's limb so that the sidearms extend from opposite sides of the patient's afflicted joint. The joint device includes a selectively actuated one-way clutch, which is preferably a sprague clutch. The clutch may be engaged for operation in a "treatment mode" or disengaged for operation in a "free-wheeling mode."

In the treatment mode, the joint device allows (but does not urge) the sidearms to move freely in the afflicted direction. Movement in the opposite or non-afflicted direction is prevented. Thus, if a patient suffers from an inability to extend his limb, the one-way clutch allows the patient to extend his arm, but prevents his contracting the arm. In this manner, the patient's arm remains at the outer limit of the patient's range of motion, with the patient free to enlarge (but not contract) that range.

In the free-wheeling mode, the joint device allows the sidearms to pivot freely in both directions so that the patient can freely extend and flex his limb to the extent that the patient is able. In the free-wheeling mode, the patient's limb can be moved either for the patient's comfort or to allow the patient to engage in therapeutic exercise without removing the joint device.

It should be noted that even in the treatment mode, the joint device does not urge the patient's limb in any one direction. Rather, the inhibition of movement is "passive", meaning that the joint device only inhibits movement when the patient applies force in the inhibited direction.

As indicated, the joint device includes a one-way clutch. By the term "one-way clutch," it is meant an overrunning clutch that is free-wheeling in one direction, while preventing or resisting movement in the other direction.

Unlike a ratchet or other similar devices, the one-way clutch allows the patient to move in the afflicted direction in continuous or infinitesimally small graduations. Contrastingly, a ratchet or the like allows pivotal movement in discrete steps of several or more degrees. Often, these steps are larger than the patient can comfortably take.

The joint device of the present invention has a number of significant advantages. The joint device has universal application in that a single joint can be used for preventing flexion or extension, and finally is suitable for use on any joint of the body. The hinge device can be supplied separately for subsequent attachment by a physician or other person to suitable braces, casts, splints or other structure as desired by the care provider.

DETAILED DESCRIPTION OF THE PREFERRED EMBODIMENT

Figure 1:
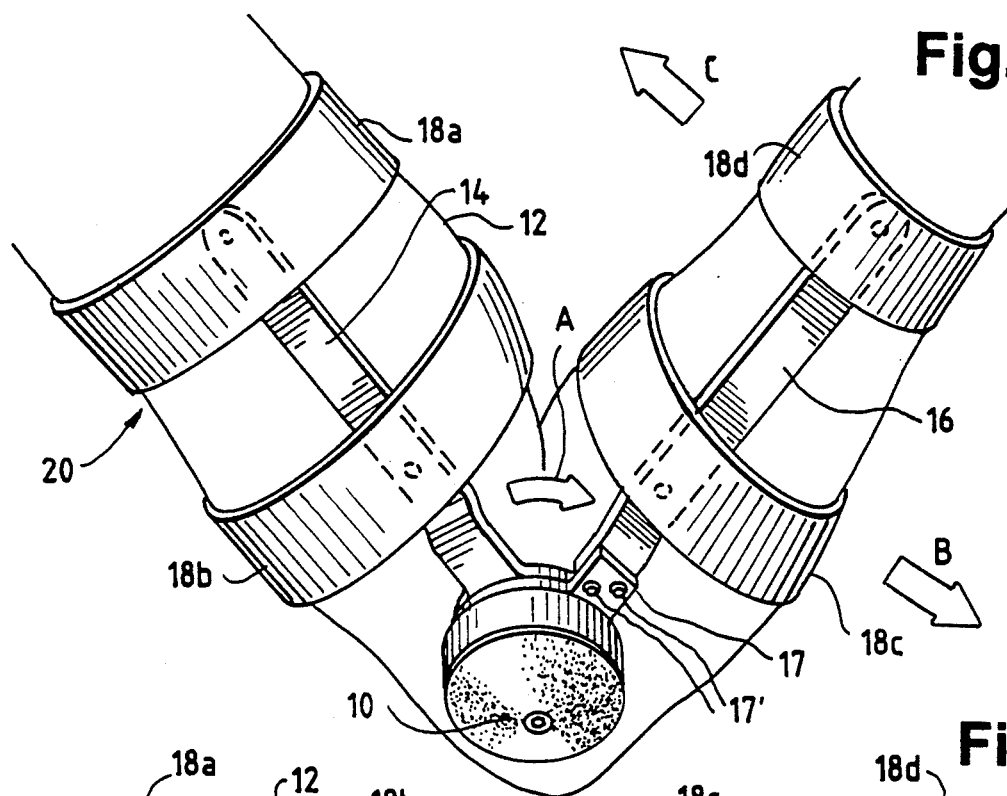
FIG. 1 is a perspective view of a joint device in accordance with a first embodiment of the invention, mounted to an arm in a flexed position.

Referring to FIG. 1, a joint device 10 in accordance with the invention is shown mounted to the lateral side of patient's right arm 12. Proximal and distal sidearms 14 and 16, respectively, extend from and are connected to joint device 10 for pivoting movement with joint device 10. A plurality of sleeves 18(a–d), secure proximal and distal sidearms 14 and 16 to patient's arm 12 to provide a splint 20.

Sleeves 18(a-d) may be of suitable elastic or leather material, and are shown by way of example only. Sidearms 14 and 16 could also be secured using a brace, plaster cast or the like.

Joint device 10 preferably has two selectively actuated modes of operation: the "treatment mode" and the "free-wheeling mode". As explained below, a mechanism is provided for switching joint device 10 between the treatment and free-wheeling modes. In the treatment mode, joint device 10 is pivotable freely in only one direction, such as, for example, shown by arrow A in FIG. 1. Movement of the patient's joint in the other direction is restricted or prevented by operation of joint device 10, as hereinafter described.

In the free-wheeling mode, the joint device 10 allows the sidearms 14 and 16 to pivot freely in both directions so that the patient can freely extend and flex his arm 12 to the extent that the patient is able. In the free-wheeling mode, the patient's limb can be moved either for the patient's comfort or to allow the patient to engage in therapeutic exercise without removing the joint device 10.

Joint device 10 is bistable, meaning that it tends to remain in one of its two modes until actively switched to the other mode by a patient or health practitioner. While it is preferable that joint device 10 have two modes of operation, only the treatment mode is essential for practicing the invention.

To better illustrate the invention, the patient is assumed to suffer from a contracture whereby the patient is unable to extend his arm 12 in the direction shown by arrow B. In the treatment mode, joint device 10 allows patient's arm 12 to extend in the direction of arrow B, but restricts contraction, that is, does not allow or resists flexion movement of arm 12 in the direction of arrow C.

When splint 20 including joint device 10 is attached to the patient, he may extend his arm as far as he is able, such, for example, as shown in FIG. 1. At this point, the patient's arm 12 is effectively immobilized: further extension of arm 12 is inhibited by the patient's ailment, and flexion is prevented or resisted by operation of the joint device 10 as hereinafter described.

It will be noted that joint device 10, while preventing or resisting flexion, does not urge patient's arm 12 toward extension. Over time, however, arm 12 will be gradually extended by the patient's own activities and/or active and forced movement by a health practitioner. In the treatment mode, joint device 10 allows such extension. However, each time patient extends his arm 12 further, joint device 10 prevents the patient's arm 12 from contracting. In this manner, the patient's range of extension is increased, until the patient is able to fully or maximally extend his arm 12, as shown in FIG. 2.

Figure 2:
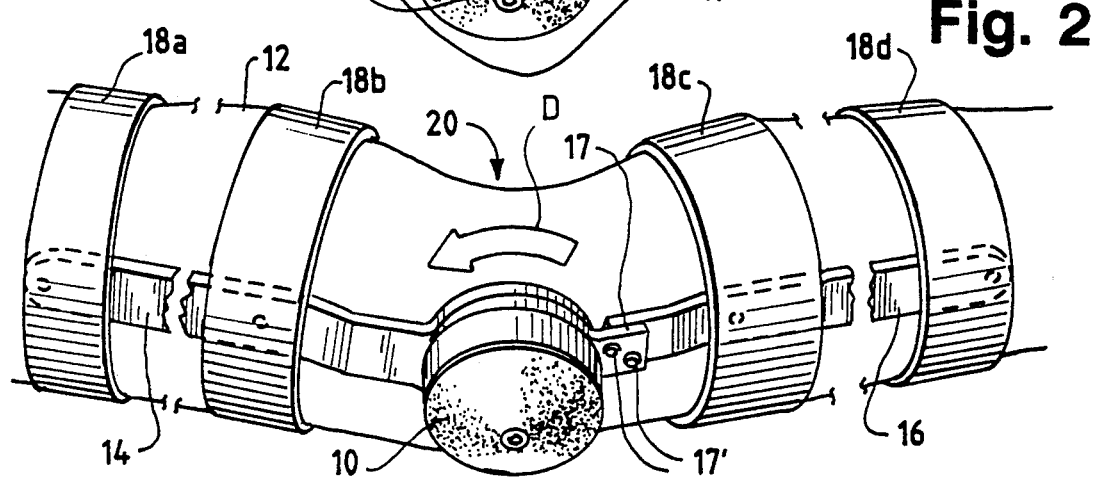
FIG. 2 is the perspective view of the joint device shown in FIG. 1, illustrating the arm in an extended position.

Joint device 10 includes a one-way clutch, preferably a sprague clutch, to allow pivoting between sidearms 14 and 16 in a single 'direction such as direction A (as shown in FIG. 1) or direction D (as shown in FIG. 2), as desired in treating a patient. For clarity, the direction arrows A and D show the pivoting motion of distal sidearm 16 with respect to proximal sidearm 14. For example, if joint device 10 allows pivoting only in direction D, then it could be used to treat a patient who can extend but cannot flex his arm 12.

The free-wheeling mode of joint device 10 can be actuated when first applying splint 20. Additionally, a patient or health practitioner may actuate the free-wheeling mode while wearing splint 20 in the event that the patient becomes uncomfortable or needs movement in the restricted direction, for example.

Figure 3:
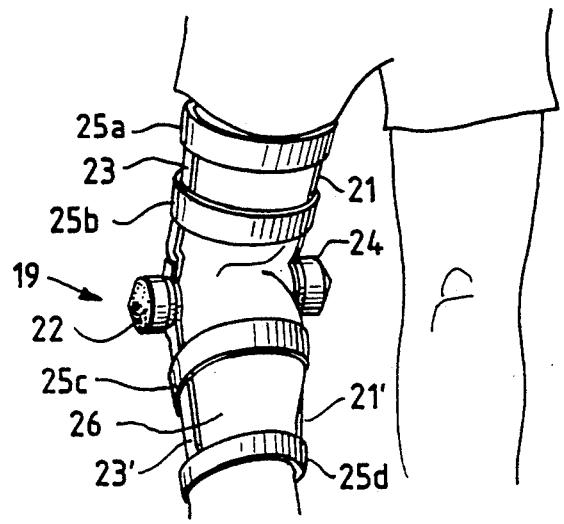
FIG. 3 is a perspective view of the joint device of FIG. 1, mounted to a patient's leg.

Referring to FIG. 3, another embodiment of a splint in accordance with the present invention is illustrated. Leg splint 19 includes joint devices 22 and 24, which are lateral and medial, respectively, and is applied to a patient's leg 26 in the same manner as splint 20 is applied to arm 12. Dual splint 19 includes a pair of medial sidearms 21 and 21' and lateral sidearms 23 and 23' with medial sidearms 21 and 21' being of the same construction as lateral sidearms 23 and 23', respectively, and suitable elastic sleeves 25(a-d) attached to the medial and lateral sidearms for securing splint 19 to the patient.

FIG. 3 illustrates two aspects of practicing the invention. First, in some cases, it is desirable to use a dual-jointed splint having a joint device on each of the medial and lateral sides of the patient's limb for additional support, stability and strength. In these embodiments, at least one of the joint devices needs to include a one-way clutch. The other joint device may be free-wheeling in both directions, that is, may operate without a treatment mode.

In the illustrated embodiment, joint device 22 has a one-way clutch for free-wheeling and treatment modes, as joint device 10, and joint device 24 is free-wheeling in both directions. Thus, joint device 24 can be constructed as joint device 10 without the one way clutch, for example. Alternatively, both joint devices 22 and 24 could have treatment and free-wheeling modes in the same direction.

Second, joint device 10 is not limited to use on arms and elbows, but rather can be applied to limbs and joints throughout the body, including legs, backs, necks, hands and feet, for example. While the present invention is intended for humans, it may also be used on animals.

Joint device 10 may be constructed in a number of ways so long as it performs in accordance with the invention as described above. Specifically, joint device 10 must be capable of operating in a treatment mode wherein joint device 10 allows the patient's limb to freely move only in the afflicted one of the extension and flexion directions, while preventing or resisting movement in the other direction. Preferably, joint device 10 also has a selectively actuated free-wheeling mode in which both extension and flexion movement is allowed.

Figure 4:
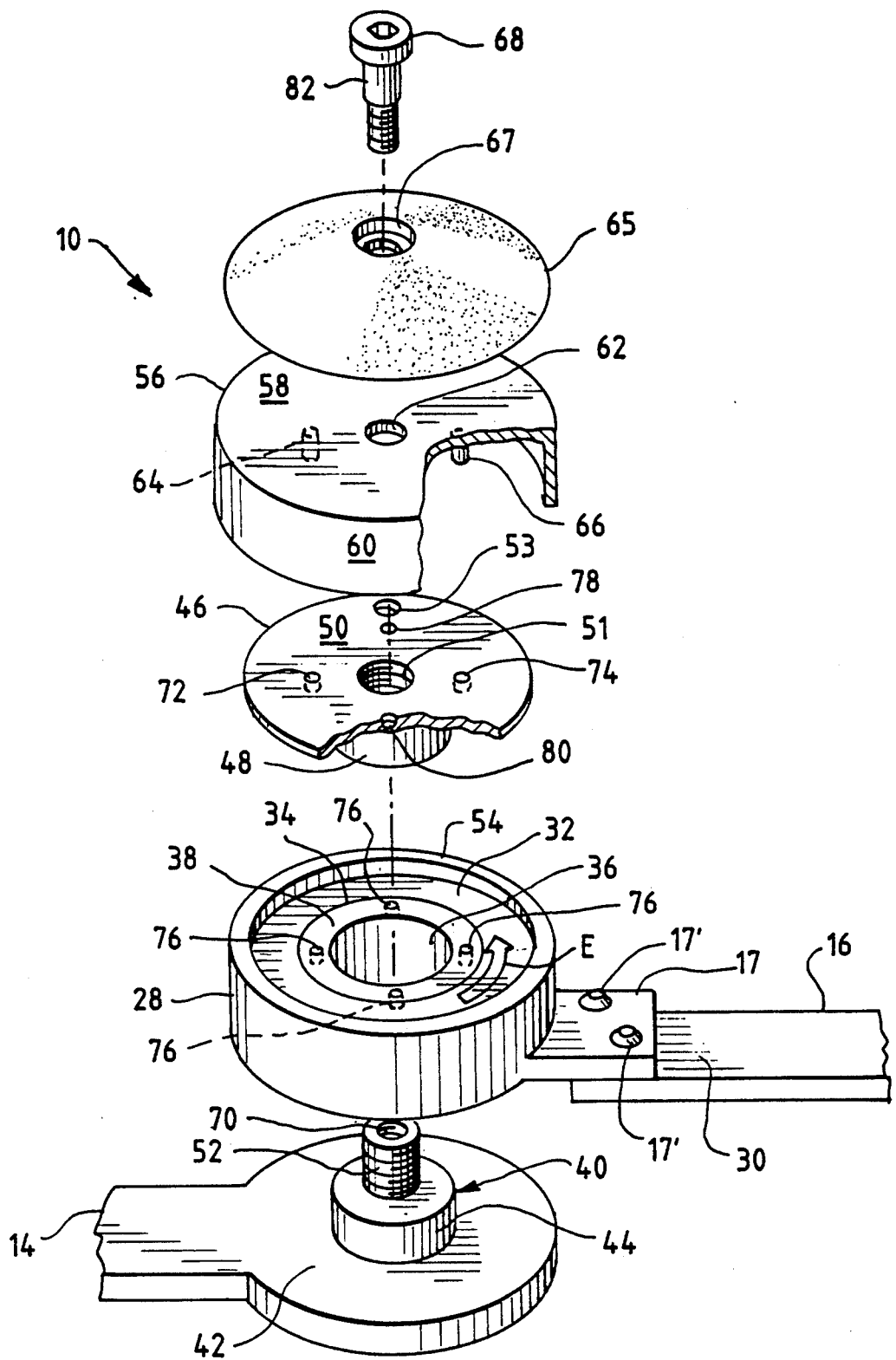
FIG. 4 is an exploded partial perspective view of the joint device shown in FIG. 1.

Referring to FIG. 4, the preferred embodiment of joint device 10 is illustrated. Joint device 10 includes an annular clutch housing 28 which is rigidly secured by any suitable means to an end 30 of distal sidearm 16. A one-way clutch 32 resides in clutch housing 28, and includes a cylindrical inner race 34 which defines a cylindrical aperture 36, and an outer race 35 located at the perimeter of clutch 32.

Figure 6:
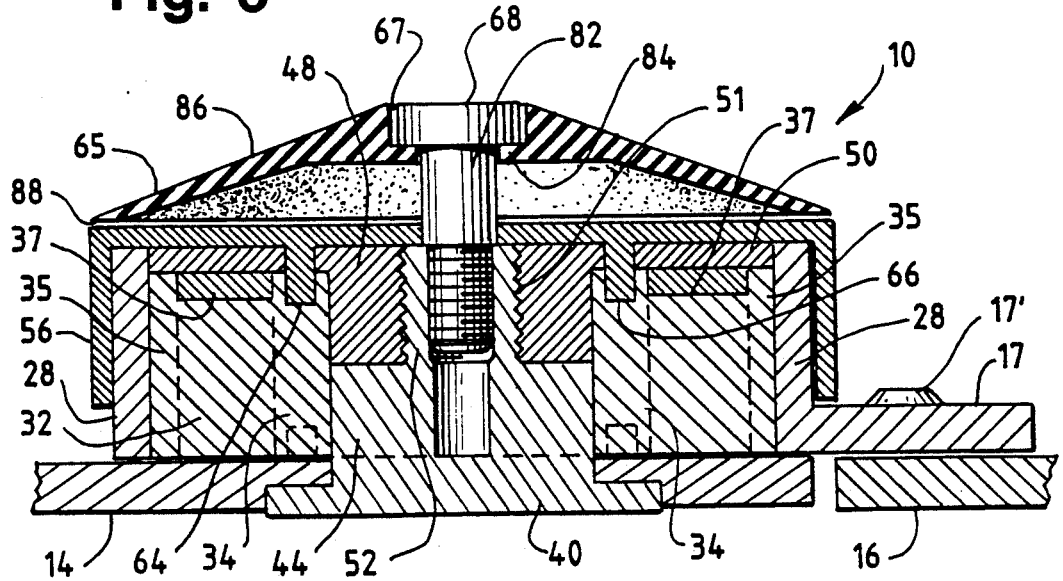
FIG. 6 is a sectional view taken along the lines 6—6 of the joint shown in FIG. 5.

Inner race 34 is rotatable in a single direction (illustrated by arrow E) about the axis of cylindrical aperture 36. It will be noted that this particular direction E is shown by way of example only. The top surface of inner race 34 defines a flat, ring shaped surface 38. Outer race 35 is not rotatable and is glued to housing 28. For clarity, outer race 35 is illustrated in FIG. 6 but not in FIG. 4.

One-way clutch 32 is preferably a commercially available sprague clutch, and is fixedly disposed within clutch housing 28 so that the longitudinal axis of cylindrical aperture 36 is normal to the longitudinal extent of distal sidearm 16.

Alternatively, one-way clutches that provide the desired restriction and movement of joint device 10 can be utilized in place of a sprague clutch, such as a ramp and roller one-way clutch, a one-way mechanical diode clutch. In some embodiments, the clutch may allow free movement in one direction and may resist (as opposed to completely prohibit) movement in the other direction.

The advantage of using a one-way clutch is that the patient may move his limb in continuous, infinitesimally small graduations. Conversely, a ratchet and pawl mechanism is less desirable because it requires the patient to move his limb in graduations which may be too coarse (albeit even only a few degrees). In some cases, the patient using a ratchet-type device may be unable to comfortably move his arm from one graduation to the next.

Joint device 10 also includes an inner bushing 40, which is rigidly secured by any suitable means to an end 42 of proximal sidearm 14. Inner bushing 40 extends in a direction normal to the longitudinal extent of proximal sidearm 14, and includes a first journal portion 44 which is sized to fit coaxially within cylindrical aperture 36. To assemble joint device 10, first journal portion 44 is disposed in cylindrical aperture 36 for rotatable bearing engagement with inner race 34.

Distal sidearm 16 is connected to a stub 17 extending from housing 28 by means of threaded fasteners 17'. Proximal sidearm 14 could also be configured as distal sidearm 16 and connected in a manner similar to distal sidearm 14, with end 42 of proximal sidearm 14 terminating in a stub (not shown) similar to stub 17.

Sprague clutch 32 and inner bushing 40 are coupled together by means of a flanged bushing 46, which includes a second journal portion 48 depending normally from a circular flange 50. Second journal portion 48 is also sized to fit coaxially within cylindrical aperture 36, and includes a threaded aperture 51 for receiving a threaded mandrel 52 which extends from first journal portion 44, as best seen in FIG. 6.

Figure 5:
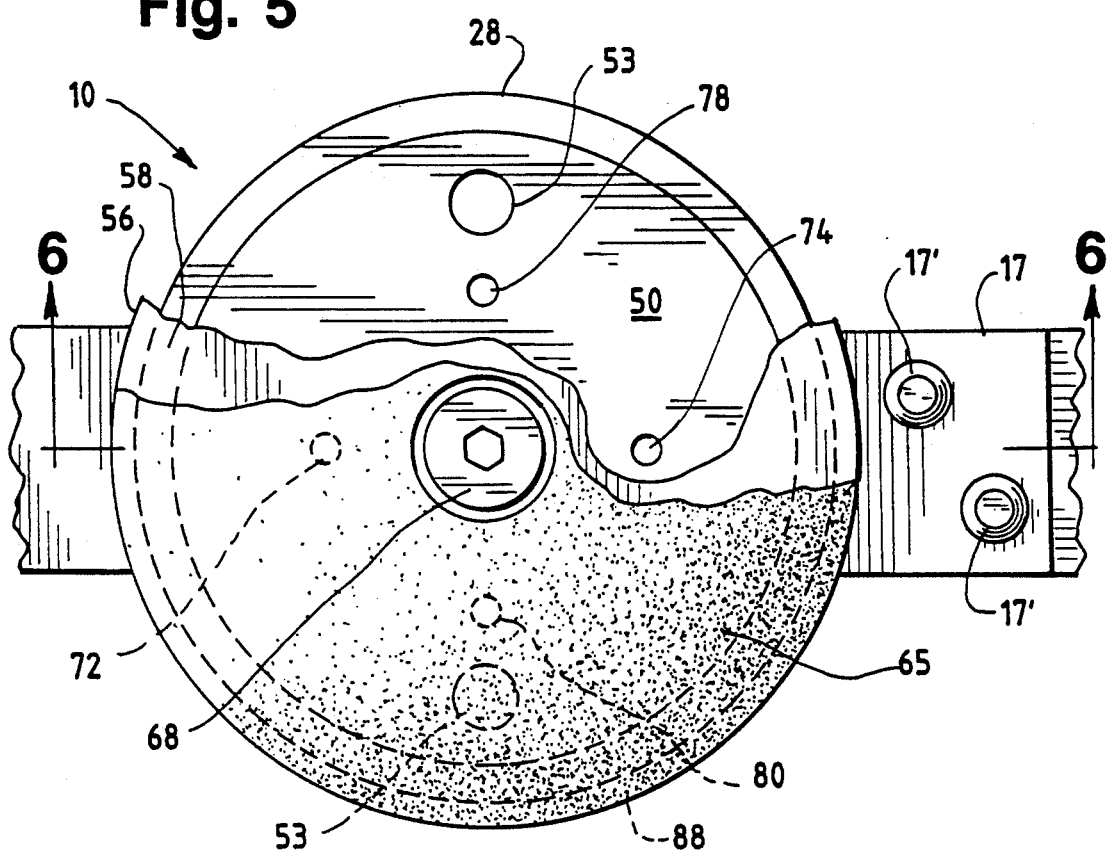
FIG. 5 is a cut-away top view of the joint device shown in FIG. 1.

Circular flange 50 is of a diameter slightly smaller than one-way clutch housing 28, as best seen in FIGS. 5 and 6. Two holes 53 may be provided in circular flange 50 to accommodate a spacer wrench or the like which can be used to screw flanged bushing 46 into inner bushing 40.

Second journal portion 48 is disposed in cylindrical clutch aperture 36 so that aperture 51 receives threaded mandrel 52. In this position, second journal portion 48 is placed in rotatable bearing engagement with inner race 34, and circular flange 50 is placed in flush engagement with flat surface 38 of inner race 34, and the top edge of outer race 35. Preferably, flat surface 38 and the top edge of outer race 35 both extend several thousandths of an inch beyond the top portion 37 of clutch 32. As best seen in FIG. 6, this prevents circular flange 50 from abrading the top portion 37. Housing 28 may be of greater height than one-way clutch 32 to provide a lip 54 which accommodates circular flange 50.

Joint device 10 also includes an outer casing 56, which includes a circular cover 58 and a cylindrical sidewall 60. An aperture 62 extends through the center of circular cover 58, and is coaxial with cylindrical clutch aperture 36. Two pins 64 and 66 depend normally from the cover, and are located on opposing sides of and are co-linear with aperture 62. An elastomeric covering 65 having a central aperture 67 is placed over outer casing 56 for cosmetic appeal, and also to urge outer casing 56 toward flanged bushing 46, as discussed below in greater detail.

A threaded bolt 68 or other suitable securing device is inserted through apertures 62 in outer casing and aperture 51 in flanged bushing 46, and is received by a threaded aperture 70 in mandrel 52 to fasten first and second journal portions 44 and 48. Alternatively, first and second journal portions could be integrally joined. When first and second journal portions 44 and 48 are so fastened, they are maintained in cylindrical aperture 36 circular flange 50. In this manner, proximal and distal sidearms 14 and 16 are pivotally coupled.

Referring to FIGS. 4 and 5, a pair of apertures 72 and 74 extend through circular flange 50 for receiving pins 64 and 66 respectively. Likewise, inner race 34 includes four notches 76 spaced at ninety-degree intervals along its top ring-shaped surface 38. Notches 76 are sized to receive the tips of pins 64 and 66. When cover 58 is placed flush against flange 50, and pins 64 and 66 are aligned with apertures 72 and 74, pins 64 and 66 extend through flange 50 and engage respective ones of notches 76.

A pair of recesses 78 and 80 which do not extend through flange 50 are also located on circular flange 50 for receiving pins 64 and 66 respectively. Pins 64 and 66 do not engage notches 76 when they are aligned with recesses 78 and 80 because the pins 64,66 cannot extend through flange 50. Thus, when pins 64 and 66 are aligned with recesses 78 and 80, joint device 10 is placed in the free-wheeling mode.

As best seen in FIGS. 5 and 6, an elongated shank portion 82 of threaded bolt 68 allows cover 58 to be slid along shank portion 82 to and from circular flange 50. When cover 58 is slid away from flange 50, pins 64 and 66 are withdrawn from apertures 72,74 (or, as the case may be, recesses 78,80) allowing casing 56 to be freely rotated about the central axis of joint device 10. In this manner, pins 64 and 66 can be selectively aligned with either aperture pair 72,74 or recess pair 78,80. Cylindrical sidewall 60 provides a convenient gripping surface for allowing patients or doctors to manipulate casing 56.

It will be observed that the foregoing structure provides a mechanism for switching joint device 10 between the treatment and free-wheeling modes. The treatment mode is enabled when pins 64 and 66 are aligned with and inserted through apertures 72 and 74, respectively, for engagement with a pair of notches 76.

When pins 64 and 66 engage notches 76, first and second journal portions 44 and 48 are coupled to inner race 34 via flange portion 50 and pins 64 and 66. Thus coupled, first and second journal portions 44 and 48 can rotate only in the direction allowed by one-way clutch 32, placing joint device 10 in the treatment mode. The direction of the threads of threaded bolt 68 and aperture 70 must be chosen so that torque in opposition to sprague clutch 32 does not unscrew bolt 68.

Contrastingly, the free-wheeling mode is engaged when cover 58 is rotated ninety degrees to align pins 64 and 66 with recesses 78 and 80. When pins 64 and 66 are aligned with recesses 78 and 80, they cannot extend through to notches 76. In this manner, flange 50 is disengaged from sprague clutch 32, first and second journal portions 44 and 48 can rotate freely within cylindrical aperture 36, and joint device 10 is placed in the free-wheeling mode.

Referring to FIG. 6, the aperture 67 of elastomeric covering 65 includes a shoulder 84. The head of bolt 68 is sized to engage shoulder 84, and thereby secure elastomeric covering 65 to the rest of joint device 10. A conical sidewall 86 depends from the apertured top portion of elastomeric covering 65, and forms a resilient annular base 88. Annular base 88 engages cover 58 of outer casing 56, urging cover 58 toward circular flange 50. It will be observed that this urging force tends to maintain pins 64 and 66 in apertures 72,74 or recesses 78,80 (as the case may be) so that joint device 10 does not inadvertently slip from free-wheeling to treatment mode, or vice versa. Joint device 22 is constructed in the same manner as joint device 10.

The placement of pins 64 and 66 in apertures 72, 74 and recesses 78, 80, in conjunction with the urging force of elastomeric covering 65, provides for the bimodal operation of joint device 10, as described above. Thus, joint device 10, can be set in the free-wheeling mode, for example, and will remain in that mode until the patient or health practitioner sets joint device 10 to the treatment mode.

The foregoing embodiment is provided by way of illustration. Persons skilled in the art will recognize that the invention may be implemented in other ways without departing from the spirit and scope of the following claims.

We claim:

1. An orthopedic device for treating a patient who is unable to flex and extend a jointed limb through its normal range of movement about the patient's joint, comprising:

first and second sidearms;

a journal having one end projecting from said first sidearm;

a clutch housing mounted to said second sidearm;

a cylindrical clutch disposed within said clutch housing and having concentric inner and outer races, said outer race being fixed to said journal housing, said inner race being rotatable in a single direction relative to said outer race and defining a concentric cylindrical aperture, wherein said journal is disposed in said cylindrical aperture for free rotation therein, and wherein said inner race includes at least one notch;

a flange attached to said projecting end of said journal, said flange having a width greater than said cylindrical aperture to maintain said journal within said circular aperture, wherein at least a portion of said flange is adjacent to said inner race; and at least one pin depending from said flange portion for selective engagement with said notch in said inner race, wherein said engagement couples said journal via said flange to said inner race to prevent relative rotational movement between said journal and said inner race so that first and second sidearms are moveable relative to each other in only a single direction.

2. The device of claim 1 wherein said pin is selectively moveable between a first position where said pin does not engage said notch, and a second position where said pin does engage said notch.

3. The device of claim 1, wherein said flange has at least a first aperture extending therethrough and sized for receiving said pin, said flange being rotatable for placing said first flange aperture into alignment with said inner race notch; and wherein said pin is selectively insertable through said first flange aperture for engaging said notch to couple said flange to said race.

4. The device of claim 3 further comprising a casing slidably coupled to said flange for movement toward and away from said flange, said pin projecting from said casing so that said pin is insertable through said first flange aperture to engage said notch when said casing is slid toward said flange, and withdrawn from said first flange aperture when said casing is slid away from said flange.

5. The device of claim 4 wherein said flange portion includes a second aperture which does not extend completely though said flange, wherein said casing is movable to selectively place said pin into alignment for insertion into one of said first and second flange apertures, wherein when said pin is inserted into said second aperture, said pin cannot engage said inner race notch.

6. The device of claim 5 wherein said casing includes biasing means for urging said casing toward said flange.

* * * * *

UNITED STATES PATENT AND TRADEMARK OFFICE
CERTIFICATE OF CORRECTION

PATENT NO. : 5,328,446
DATED : July 12, 1994
INVENTOR(S) : William P. Bennell, et al.

It is certified that error appears in the above-indentified patent and that said Letters Patent is hereby corrected as shown below:

Col. 7, line 35, after "cylindrical" insert --one-way--.

Signed and Sealed this

Twentieth Day of September, 1994

Attest:

BRUCE LEHMAN

*Attesting Officer*        *Commissioner of Patents and Trademarks*